US008026242B2

(12) United States Patent
Carruthers et al.

(10) Patent No.: US 8,026,242 B2
(45) Date of Patent: Sep. 27, 2011

(54) CYCLOPROPYL AMINES AS MODULATORS OF THE HISTAMINE $H_3$ RECEPTOR

(76) Inventors: Nicholas I. Carruthers, Poway, CA (US); Michael A. Letavic, San Diego, CA (US)

( * ) Notice: Subject to any disclaimer, the term of this patent is extended or adjusted under 35 U.S.C. 154(b) by 0 days.

(21) Appl. No.: 13/028,351

(22) Filed: Feb. 16, 2011

(65) Prior Publication Data

US 2011/0136797 A1 Jun. 9, 2011

Related U.S. Application Data

(62) Division of application No. 11/531,849, filed on Sep. 14, 2006, now Pat. No. 7,687,499.

(60) Provisional application No. 60/717,659, filed on Sep. 16, 2005.

(51) Int. Cl.
  *C07D 413/10* (2006.01)
  *A61K 31/5377* (2006.01)
(52) U.S. Cl. ................................. 514/253.01; 544/360
(58) Field of Classification Search .................. 544/360; 514/253.01
  See application file for complete search history.

(56) References Cited

U.S. PATENT DOCUMENTS

| 3,714,179 A | 1/1973 | Tweit |
| 3,886,160 A | 5/1975 | Tweit |
| 4,668,679 A * | 5/1987 | Simond et al. ........... 514/253.01 |
| 5,030,644 A | 7/1991 | Baldwin et al. |
| 5,098,900 A | 3/1992 | Mutsukado et al. |
| 5,217,986 A | 6/1993 | Pomponi et al. |
| 5,352,707 A | 10/1994 | Pompni et al. |
| 5,464,788 A | 11/1995 | Bock et al. |
| 5,569,659 A | 10/1996 | Reitz |
| 5,681,954 A | 10/1997 | Yamamoto et al. |
| 5,756,504 A | 5/1998 | Bock et al. |
| 5,869,479 A | 2/1999 | Kreutner et al. |
| 5,883,096 A | 3/1999 | Lowe et al. |
| 5,889,006 A | 3/1999 | Lowe et al. |
| 5,900,422 A | 5/1999 | Ali |
| 6,596,706 B1 | 7/2003 | Kikuchi et al. |
| 2004/0110746 A1 | 6/2004 | Apodaca et al. |
| 2007/0066821 A1 | 3/2007 | Allison et al. |

FOREIGN PATENT DOCUMENTS

| EP | 0186817 A1 | 7/1986 |
| EP | 0624584 B1 | 8/1998 |
| EP | 0978512 A1 | 2/2000 |
| JP | 61267560 A | 11/1986 |
| JP | 02306237 A2 | 12/1990 |
| JP | HEI 10-59954 | 3/1998 |
| WO | WO 93/04684 A1 | 3/1993 |
| WO | WO 9525443 A1 | 9/1995 |
| WO | WO 9626196 A2 | 8/1996 |
| WO | WO 97 30992 A1 | 8/1997 |
| WO | WO 9805292 A2 | 2/1998 |
| WO | WO 9924475 A1 | 5/1999 |
| WO | WO 99/42458 | 8/1999 |
| WO | WO 02/012190 A2 | 2/2002 |
| WO | WO 02/012214 A2 | 2/2002 |
| WO | WO 02/20500 A2 | 3/2002 |
| WO | WO 02/024695 A2 | 3/2002 |
| WO | WO 02/062784 A1 | 8/2002 |
| WO | WO 02/076925 A2 | 10/2002 |
| WO | WO 03/004480 A2 | 1/2003 |
| WO | WO 03/024928 A2 | 3/2003 |
| WO | WO 03/024929 A1 | 3/2003 |
| WO | WO 03/0314 A1 | 4/2003 |
| WO | WO 03/050099 A1 | 6/2003 |
| WO | WO 03/055866 A1 | 7/2003 |
| WO | WO 03/064411 A1 | 8/2003 |
| WO | WO 03066604 A2 | 8/2003 |
| WO | WO 04037801 A1 | 5/2004 |
| WO | WO 2005/035534 A1 | 4/2005 |
| WO | WO 2005/040144 A1 | 5/2005 |
| WO | WO 2006/067401 A1 | 6/2006 |
| WO | WO 08015125 A1 | 2/2008 |

OTHER PUBLICATIONS

Aicher, T.D. et al.: "Secondary Amides of ®-3,3,3-Trifluoro-2-hydroxy-2-methylpropionis Acid as Inhibitors of Pyruvate Dehydrogenase Kinase"; J. Med. Chem. 2000, 43: 236-249.
Albengres, E. et al. Systemic Antifungal Agents. Drug Safety (Feb. 1998) 18(2):83-97.
Ali, S.M. et al. Design, Synthesis, and Structure-Activity Relationships of Acetylene-Based Histamine H3 Receptor Antagonists. J. Med. Chem. (1999).
Anjaneyulu, B. et al. Synthesis of 14C-Labelled 1-Methanesulphony1-3-(1-methyl-5-nitro-1$H$-imidazol-2-yl)-2-imidazolidinone, (Go 10213). J. Labelled.
Apodaca, R. et al. A New Class of Diamine-Based Histamine H3 Receptor Antagonists: 4-(Aminoalkoxy)benzylamines. J. Med. Chem. (2003) 46(18):3938-3944.
Arrang, J.-M. et al. Auto-inhibition of Brain Histamine Release Mediated by a Novel Class (H3) of Histamine Receptor. Nature (Apr. 1983) 302:832-837.
Ash, A.S.F.; Schild, H.O. Receptors Mediating Some Actions of Histamine. Br. J. Pharmac. Chemother. (1966) 27:427-439.
Augustin, M. et al.: Zeitschrift fuer Chemie 1967, 7(10), 389.
Back, D.J.; Tjia, J.F. Inhibition of Tolbutamide Metabolism by Substituted Imidazole Drugs in Vivo: Evidence for a Structure-Activity Relationship. Br. J. Pharmacol. (1985) 85:121-126.
Barbier, A.J. et al.: "Acute wake-promoting actions of JNJ-5207852, a novel, diamine-based H3 antagonist"; British J. of Pharmacology (2004) 143: 649-661.
Barn, D.R. et al.: "Synthesis of an Array of Amides by Aluminum Chloride Assisted Cleavage of Resin-Bound Esters", Tetrahedron Letters, Elsevier Science Publishers, Amsterdam, Netherlands, vol. 37(19): 3213-3216, Apr. 1996.
Barnes, J.C. et al. The Selective Histamine H3 Receptor Antagonist Thioperamide Improves Cognition and Enhances Hippocampal Acetylcholine Release In Vivo. Soc. Neurosci. Abstr. (1993) 19:1813.
Bioworld Today, Mar. 2, 1999, p. 3.
Black, J.W. et al. Definition and Antagonism of Histamine H2-Receptors. Nature (Apr. 1972) 236:385-390.

(Continued)

*Primary Examiner* — Kahsay T Habte
(74) *Attorney, Agent, or Firm* — Michael J. Atkins

(57) ABSTRACT

Certain cyclopropyl amines are histamine $H_3$ modulators useful in the treatment of histamine $H_3$ receptor mediated diseases.

5 Claims, No Drawings

OTHER PUBLICATIONS

Celanire, S. et al.: "Histamine $H_3$ receptor antagonists reach out for the clinic"; DDT (Dec. 2005) 10(23/24): 1613-1627.

Chen, Z.: "Effect of histamine $H_3$-recepor anagonst clobenpropit on spatial memory of radial maze performance in rats"; Acta Pharmacol Sin (2000) 21(10): 905-910.

Ding, Y.-S. et al. Synthesis of High Specific Activity (+)- and (–)-6-[18F]Fluoronorepinephrine via the Nucleophilic Aromatic Substitution Reaction. J. Med. Chem. (1991) 34(2)3767-771.

Erdelyi, M.; Gogoll, A. Rapid Homogeneous-Phase Sonogashira Coupling Reactions Using Controlled Microwave Heating. J. Org. Chem. (2001).

Fox, G.B. et al.: "Effects of histamine $H_3$ receptor ligands GT-2331 and ciproxifan in a repeated acquisition avoidance response in the spontaneously hypertensive rat pup"; Behavioural Brain Research 131 (2002): 151-161.

Ganellin, C.R. et al. Synthesis of Potent Non-Imidazole Histamine H3-Receptor Antagonists. Arch. Pharm. Pharm. Med. Chem. (Weinheim, Ger.) (1998) 331:395-404.

Garbarg, M. et al. S-[2-(4-Imidazolyl)ethyl]isothiourea, a Highly Specific and Potent Histamine H3 Receptor Agonist. J. Pharmacol. Exp. Ther. (1992).

Gillaspy, M.L. et al.: "A Simple Method for the Formation of Cyclopropylamines: The First Synthesis of Tricyclopropylamine"; Tetrahedron Letters (1995) 36(41): 7399-7402.

Gliatech Inc. Press Release Nov. 5, 1998.

Gonzalez, F. Garcia, et al. Synthesis of 3-aryl(alkyl)-4-(D-*arabino*-tetrahydroxybutyl)imidazolin-2-thiones, Carbohydrate Research, 22 (1972): 436-440.

Hancock, A.A.: "The challenge of drug discovery of a GPCR target: Analysis of preclinical pharmacology of histamine $H_3$ antagonists/inverse agonists"; Elsevier Biochem. Pharmacology (2006) 71: 1103-1113.

Hirt, R. et al.: Experientia 1961, 17, 418-20.

Ichinose, M.; Barnes, P.J. Histamine H3-Receptors Modulate Nonadrenergic Noncholinergic Neural Bronchoconstriction in Guinea-Pig in Vivo. Eur. J. Pharmacol. (1989) 174(1):49-55.

Iemura, R. et al. Synthesis of Benzimidazole Derivatives as Potential H1—Antihistaminic Agents. J. Heterocycl. Chem. (1987) 24:31-37.

Imamura, M. et al. Unmasking of Activated Histamine H3-Receptors in Myocardial Ischemia: Their Role as Regulators of Exocytotic Norepinephrine Release. J. Pharmacol. Exp. Ther. (1994) 271(3):1259-1266.

Ireland-Denny, L. et al.: "Species-related pharmacological heterogeneity of histamine $H_3$ receptors"; Elsevier European J. of Pharmacology 433 (2001): 141-150.

Iwata, R. et al. Synthesis of 3-[1*H*-Imidazol-4-yl]propyl 4-[18F]fluorobenzyl Ether ([18F]Fluoroproxyfan): A Potential Radioligand for Imaging Histamine H3 Receptors. J. Labelled Compd. Radiopharm. (2000) 43:873-882.

Jarosinski, M.A.; Anderson, W.K. Preparation of Noncondensed 2-Substituted 1-Methylimidazoles via Ipso Substitution Reaction on 2-Sulfinyl or 2-Sulfonyl Derivatives of 4,5-Disubstituted 1-Methylimidazoles. J. Org. Chem. (1991) 56(12):4058-4062.

Jones, R.G. Studies on Imidazoles. II. The Synthesis of 5-Imidazolecarboylates fromGlycine and Substituted Glycine Esters. J. Am. Chem. Soc. (1949) 71:644-647.

Jordaan, A., Arndt, R.R., The Synthesis of 1-Methyl-5-(α-indolyl)imidazole and 1-Methyl-2-ethylthiol-5-(α-indolyl)imidazole. Journal of Heterocyclic Chemistry 5(5), 723-5 (English) 1968.

Kapetanovic, I.M.; Kupferberg, H.J. Nafimidone, an Imidazole Anticonvulsant, and Its Metabolite as Potent Inhibitors of Microsomal Metabolism of Phenytoin and Carbamazepine. Drug Metab. Dispos. (1984) 12(5):560-564.

Korte, A. et al. Characterization and Tissue Distribution of H3 Histamine Receptors in Guinea Pigs by N alpha-Methylhistamine. Biochem. Biophys. Res. Commun. (May 1990) 168(3):979-986.

Krause, M. et al. Medicinal Chemistry of Histamine H3 Receptor Agonists; In the Histamine H3 Receptor—A Target for New Drugs Leurs, R.; Timmerman, H. (Eds.) Elsevier (1998) 175-196.

Lamberti, C. et al.: "Antidepressant-like effects of endogenous histamine and of two histamine $H_1$ receptor agonists in the mouse forced swim test"; British J. of Pharmacology (1998) 123: 1331-1336.

Lavrijsen, K. et al. Induction Potential of Antifungals Containing an Imidazole or Triazole Moiety. Biochem. Pharmacol. (1986) 35(11):1867-1878.

Leurs, R. et al. The Medicinal Chemistry and Therapeutic Potentials of Ligands of the Histamine H3 Receptor. Prog. Drug Res. (1995) 45:107-165.

Leurs, R. et al; "Therapeutic potential of histamine H3 recepto agonists and antagonitsts" Trends n. Pharmacological sciences, Elsevier Trends Journal, Cambridge, BG, vol. 19, No. 5, 1 May 1998; pp. 177-183.

Lin, J.-S. et al. Involvement of Histaminergic Neurons in Arousal Mechanisms Demonstrated with H3-Receptor Ligands in the Cat. Brain Res. (1990) 523:325- 330.

Linney, I.D. et al. Design, Synthesis, and Structure-Activity Relationships of Novel Non-Imidazole Histamine H3 Receptor Antagonists. J. Med. Chem. (2000) 43(12):2362-2370.

Love, P. et al.: "Polar Substituent Effects in Gas-Phase Lewis Acid-Base Equilibria. I. Intrinsic Basicity of Amines1"; J. of the Am. Chem. Society (May 1968) 90(10): 24552462.

Lovenberg, T.W. et al. Cloning and Functional Expression of the Human Histamine H3 Receptor. Mol. Pharmacol. (1999) 55:1101-1107.

Lovenberg, T.W. et al. Cloning of Rat Histamine H3 Receptor Reveals Distinct Species Pharmacological Profiles. J. Pharmacol. Exp. Ther. (2000) 293(3):771-778.

Machidori, H. et al. Zucker Obese Rats: Defect in Brain Histamine Control of Feeding. Brain Res. (1992) 590:180-186.

McLeod, R.L. et al. Antimigraine and Sedative Activity of SCH 50971: A Novel Orally-Active Histamine H3 Receptor Agonist. Soc. Neurosci. Abstr. (1996) 22:2010.

Meier, G. et al. Piperidino-Hydrocarbon Compounds as Novel Non-Imidazole Histamine H3-Receptor Antagonists. Bioorg. Med. Chem. (2002) 10:2535-2542.

Miyazaki, S. et al.: "Effects of Thioperamide, a Histamine $H_3$-receptor Antagonist, on a Scopolamine-induced Learning Deficit Using an Elevated Plus-maze Test in Mice"; Life Sciences, (1995) 57(23): 2137-2144.

Miyazaki, S. et al.: "Effects of Thioperamide on the Cholinergic System and the Step-Through Passive Avoidance Test in Mice"; Meth Find Exp Clin Pharmacol (1995) 17(10): 653-658.

Monti, J.M. et al. Effects of Selective Activation or Blockade of the Histamine H3 Receptor on Sleep and Wakefulness. Eur. J. Pharmacol. (1991) 205(3):283-287.

Morisset, S. et al. High Constitutive Activity of Native H3 Receptors Regulates Histamine Neurons in Brain. Nature (Dec. 2000) 408:860-864.

Nakamura, M. et al.: "The Preparation of Oligo(ethylenepiperazine)'s and the Polyamine-polyamides Thereof"; Kenkyu Hokoku—Asahi Garasu Kogyo Gijutsu Shoreikai (1973) 23: 297-308.

Oda, T. et al. Molecular Cloning and Characterization of a Novel Type of Histamine Receptor Preferentially Expressed in Leukocytes. J. Biol. Chem. (2000) 275(47):36781-36786.

Ohta, S. et al. Synthesis and Application of Imidazole Derivatives. Introduction of Carbogenic Substituents into the 5-Position of 1-Methyl-1*H*-imidazole. Chem. Pharm. Bull. (1992) 40(10):2681-2685.

Orsetti, M. et al.: "Histamine $H_3$-receptor antagonism improves memory retention and reverses the cognitive deficit induced by scopolamine in a two-trial place recognition task"; Elsevier Behavioural Brain Research 124 (2001): 235-242.

Ortho-McNeil Pharmaceutical, Inc. (WO03050099): Phenylalkynes to Treat Histamine-Mediated Conditions. Expert Opin. Ther. Patents (2003).

Panula, P. et al. Significant Changes in the Human Brain Histaminergic System in Alzheimer's Disease. Soc. Neurosci. Abstr. (1995) 21:1977.

Perez-Garcia, C. et al.: "Effects of histamine $H_3$ receptor ligands in experimental models of anxiety and depression"; Psychopharmacology (1999) 142: 215-220.

Phelps, M.E. Positron Emission Tomography Provides Molecular Imaging of Biological Processes. Proc. Natl. Acad. Sci. (2000) 97(16):9226-9233.

Phillips, B.T. et al. Preparation of 5-Substituted 2-Mercapto-1-methylimidazoles. Direct Metalation of 2-Mercapto-1-methylimidazole. Synthesis (1990) :761-763.

Phillips, J.G.; Ali, S.M. Medicinal Chemistry of Histamine $H_3$ Receptor Antagonists; in the Histamine H3 Receptor—A Target for New Drugs Leurs, R.; Timmerman, H. (Eds.) Elsevier (1998) 197-222.

Phillips, J.G. et al. Chapter 4, Recent Advances in Histamine H3 Receptor Agents. Ann. Reports in Med. Chem., 31, 1998, pp. 31-40.

Rouleau, A. et al. Bioavailability, Antinociceptive and Antiinflammatory Properties of BP 2-94, a Histamine H3 Receptor Agonist Prodrug. J. Pharmacol.

Sabbatini, Renato,M.E., The Cyclotron and PET. In Brain & Mind an electronic magazine about Neuroscience [online], Mar., 1997. Retrived from the internet, <http:www.epub.org.br/cm/n01/pet/petcyclo.htm.

Schlicker, E.; Marr, I. The Moderate Affinity of Clozapine at H3 Receptors Is Not Shared by Its Two Major Metabolites and by Structurally Related and Unrelated Atypical Neuroleptics. Naunyn-Schmiedeberg's Arch. Pharmacol. (1996) 353:290-294.

Schnettler, R.A. et al. 4-Aroyl-1,3-dihydro-2$H$-imidazol-2-ones, a New Class of Cardiotonic Agents. J. Med. Chem. (1982) 25:1477-1481.

Shapiro, G.; Marzi, M. Synthesis of 2,5-Dilithio-1-methylimidazole. Tetrahedron Lett. (1993) 34(21):3401-3404.

Sheets, J.J.; Mason, J.I. Ketoconazole: a Potent Inhibitor of Cytochrome P-450- Dependent Drug Metabolism in Rat Liver. Drug Metab. Dispos. (1984) 12(5):603-606.

Stark, H. Recent Advances in Histamine H3/H4 Receptor Ligands. Expert Opin. Ther. Patents (2003) 13(6):851-865.

Stark, H. et al. Developments of Histamine H3-Receptor Antagonists. Drugs Future (1996) 21(5):507-520.

Tozer, M.J., et al.: "From Histamine to imidazolylalkyl-sulfonamides: the design of a novel series of histamine H3 receptor antagonists"; Bioorganic & Medicinal CHemistry Letters, Oxford, GB, vol. 9, No. 13, Jul. 5, 1999, pp. 1825-1830, XP004168846.

Tozer, M.J.; Kalindjian, S.B. Histamine H3 Receptor Antagonists. Exp. Opin. Ther. Patents (2000) 10(7):1045-1055.

Walczynski, K. et al. Non-Imidazole Histamine H3 Ligands, Part 2: New 2-Substituted Benzothiazoles as Histamine H3 Antagonists. Arch. Pharm. Pharm. Med. Chem. (Weinheim, Ger.) (1999) 332:389-398.

Walczynski, K. et al. Non-Imidazole Histamine H3 Ligands. Part I. Synthesis of 2-(1-Piperazinyl)- and 2-(Hexahydro-1H-1,4-diazepin-1-yl)benzothiazole Derivatives as H3-Antagonists with H1 Blocking Activities. Farmaco (1999) 54:684-694.

West, R.E. et al. Identification of Two H3-Histamine Receptor Subtypes. Mol. Pharmacol. (1990) 38(5):610-613.

West, R.E., Jr. et al. The Profiles of Human and Primate [3H]N alpha-methylhistamine Binding Differ from That of Rodents. Eur. J. Pharmacol. (1999).

Yokoyama, H. et al. Effect of Thioperamide, a Histamine H3 Receptor Antagonist, on Electrically Induced Convulsions in Mice. Eur. J. Pharmacol. (1993) 234:129-133.

Zaragoza, F. et al.: "1-Alkyl-4-acylpiperazines as a New Class of Imidazole-Free Histamine $H_3$ Receptor Antagonists"; J. Med. Chem. (2004) 47: 2833-2838.

Zaragoza, F. et al.: "2-(4-Alkylpiperazin-1-yl)quinolines as a New Class of Imidazole-Free Histamine $H_3$ Receptor Antagonists"; J. Med. Chem. (2005) 48: 306311.

Applicant's Letter dated Aug. 26, 2006 citing 3D-Pharmaceuticals Ex #43.

Berge, S.M. et al.: "Pharmaceutical Salts"; J. of Pharmaceutical Sciences (1977) 66(1): 1-19.

Ibrahim, El Sebai A. et al.: "Synthesis of 4-Substituted Aminobenzoate Quaternary Salts as Potent Antispasmodic Agents"; J. of Pharmaceutical Sciences (1979) 68(3): 332-335.

Miocque, Marcel et al.: "Derivatives of Imipramine: Aminomethylation of Diphenylamine and of Iminodibenzyl"; Eur. J. Med. Chem.—Chimica Therapeutica, (May-Jun. 1977) 12(3): 219-225. Note: Copy of English-language translation is attached.

Altana Pharma AG et al. V. Teva Pharmaceuticals Inc, et al. (FED. CIR. 2008-1039 May 14, 2009).

Gavezotti et al "Are Crystal Structures Predictable?" Accounts of Chemical Research 1994 vol. 27 pp. 309-314.

Vippagunta et al "Crystalline Solids" Advanced Drug Delivery Reviews 2001 vol. 48 pp. 3-26.

PCT International Search Report dated Mar. 31, 2004 for PCT International Application No. PCT/US03/33343.

International Search Report dated May 28, 2009 for PCT Application No. PCT/US2006/035877.

Greene et al., Protective Groups in Organic Synthesis 34D Ed John Wiley & Sons 1999.

Leurs et al., the Histamine H3 Receptor a Target for New Drugs Leurs R. And Timmerman H. Eds Elsevier 1998.

Mcomie et al., Protective Groups in Organic Chemistry Ed. J.F.W. Mcomie Plenum Press 1973.

Stahl et al., Handbook of Pharmaceutical Salts, Properties, Selection and Use Stahl P.H. Wermuth C.G. Eds. Wiley-VCH and VHCA Zurich 2002.

Bundgaard Design of Prodrugs H Bundgaard Elsevier 1985.

* cited by examiner

CYCLOPROPYL AMINES AS MODULATORS OF THE HISTAMINE H₃ RECEPTOR

RELATED APPLICATIONS

This application is a divisional of U.S. Ser. No. 11/531,849 filed on Sep. 14, 2006 now U.S. Pat. No. 7,687,499, which claims the benefit under 35 USC §119(e) of the following provisional application: U.S. Ser. No. 60/717,659 filed on Sep. 16, 2005. The complete disclosures of the aforementioned related U.S. patent applications are hereby incorporated herein by reference for all purposes.

FIELD OF THE INVENTION

The present invention relates to a series of cyclopropyl amines, their synthesis, and methods for using them to treat disorders and conditions in which the histamine $H_3$ receptor is involved. As a consequence of these activities, the compounds of the present invention will have therapeutic utility for the treatment of a variety of CNS related disorders including, but not limited to, narcolepsy, sleep disorders, obesity, neurodegenerative disorders, cognitive disorders, and hyperactivity disorders.

BACKGROUND OF THE INVENTION

Histamine {2-(imidazol-4-yl)ethylamine} is a biologically-active molecule. Histamine exerts a physiological effect via multiple distinct G-protein coupled receptors. The histamine $H_3$ receptor was first described as a presynaptic autoreceptor in the central nervous system (CNS) (Arrang, J.-M. et al., Nature 1983, 302, 832-837) controlling the synthesis and release of histamine. Evidence has emerged showing that $H_3$ receptors are also located presynaptically as heteroreceptors on serotonergic, noradrenergic, dopaminergic, cholinergic, and GABAergic (gamma-aminobutyric acid containing) neurons. These $H_3$ receptors have also recently been identified in peripheral tissues such as vascular smooth muscle. Consequently, there are many potential therapeutic applications for histamine $H_3$ agonists, antagonists, and inverse agonists. (See: "The Histamine $H_3$ Receptor-A Target for New Drugs", Leurs, R. and Timmerman, H., (Eds.), Elsevier, 1998; Morisset, S. et al., Nature 2000, 408, 860-864.)

Several indications for histamine $H_3$ antagonists and inverse agonists have similarly been proposed based on animal pharmacology and other experiments with known histamine $H_3$ antagonists (e.g. thioperamide). These include dementia, Alzheimer's disease (Panula, P. et al., Soc. Neurosci. Abstr. 1995, 21, 1977), epilepsy (Yokoyama, H. et al., Eur. J. Pharmacol. 1993, 234, 129-133), narcolepsy, with or without associated cataplexy, cataplexy, disorders of sleep/wake homeostasis, idiopathic somnolence, excessive daytime sleepiness (EDS), circadian rhythm disorders, sleep/fatigue disorders, fatigue, drowsiness associated with sleep apnea, sleep impairment due to perimenopausal hormonal shifts, jet lag, Parkinson's-related fatigue, multiple sclerosis (MS)-related fatigue, depression-related fatigue, chemotherapy-induced fatigue, eating disorders (Machidori, H. et al., Brain Res. 1992, 590, 180-186), motion sickness, vertigo, attention deficit hyperactivity disorders (ADHD), learning and memory (Barnes, J. C. et al., Soc. Neurosci. Abstr. 1993, 19, 1813), and schizophrenia (Schlicker, E. and Marr, I., Naunyn-Schmiedeberg's Arch. Pharmacol. 1996, 353, 290-294). (Also see: Stark, H. et al., Drugs Future 1996, 21 (5), 507-520; and Leurs, R. et al., Prog. Drug Res. 1995, 45, 107-165 and references cited therein.) Histamine $H_3$ antagonists, alone or in combination with a histamine $H_1$ antagonist, are reported to be useful for the treatment of upper airway allergic responses (U.S. Pat. Nos. 5,217,986; 5,352,707 and 5,869,479). A more recent review of this topic was presented by Tozer and Kalindjian (Exp. Opin. Ther. Patents 2000, 10, 1045). For additional reviews, see: Celanire, S. Drug Discovery Today 2005, 10 (23/24), 1613-1627; Hancock, A. A. Biochem. Pharmacol. 2006, 71, 1103-1113.

The compounds of the present invention display potency at the human $H_3$ receptor as determined by receptor binding to the human histamine $H_3$ receptor (see Lovenberg, T. W. et al., Mol. Pharmacol. 1999, 55, 1101-1107). Screening using the human receptor is particularly important for the identification of new therapies for the treatment of human disease. Conventional binding assays, for example, are determined using rat synaptosomes (Garbarg, M. et al., J. Pharmacol. Exp. Ther. 1992, 263 (1), 304-310), rat cortical membranes (West, R. E. et al., Mol. Pharmacol. 1990, 38, 610-613), and guinea pig brain (Korte, A. et al., Biochem. Biophys. Res. Commun. 1990, 168 (3), 979-986). Only limited studies have been performed previously using human tissue or the human receptor, but these indicate significant differences in the pharmacology of rodent and primate receptors (West, R. E. et al. Eur. J. Pharmacol. 1999, 377, 233-239; Ireland, D. et al. Eur. J. Pharmacol. 2001, 433, 141-150).

To achieve a desired pharmacological effect, a compound must display potency against the biological target, as well as a suitable pharmacokinetic profile. First, the compound must be able to travel to its site of action, whether in the CNS, requiring adequate permeation of the blood-brain barrier, or in the periphery. Absorption through various biological membranes is dependent on the physical properties of the drug (degree of ionization at physiological pH, partition coefficient, molecular size, among other factors). Once the desired pharmacological effect is produced, a drug must be eliminated from the organism at a suitable rate. Where an elimination process is too slow, an accumulation of the drug can occur, potentially causing undesirable side effects.

Various $H_3$-mediated diseases may require compounds with distinct and different pharmacokinetic profiles. In particular, administration of a compound with a short half-life provides greater control over exposure and duration of action of the drug, which may be advantageous in treating or preventing a particular disease or condition. A compound with such an optimized profile allows for the use of tailored formulations, dosing regimens, and/or delivery strategies to accomplish these results. For example, a compound with an attenuated pharmacokinetic profile may produce a shorter pharmacodynamic effect, which may be preferable in treating certain disease states. In contrast, a compound with a long half-life may be preferred for conditions in which constant occupancy of the target by the drug, with no or only very minor changes in drug concentration, are desirable.

Various piperazinyl benzamides were disclosed in U.S. Patent Appl. Publication No. US-2004-0110746-A1 (Jun. 10, 2004), which is hereby incorporated by reference.

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety.

Described herein is a series of N-cyclopropyl amine compounds with the ability to modulate the activity of the histamine receptor, specifically the $H_3$ receptor.

SUMMARY OF THE INVENTION

The invention features a compound selected from the group consisting of: (4-cyclopropyl-piperazin-1-yl)-(4-morpholin-4-ylmethyl-phenyl)-methanone, (4-cyclopropyl-piperazin-1-yl)-[4-(4-fluoro-piperidin-1-ylmethyl)-phenyl]-methanone, (4-cyclopropyl-piperazin-1-yl)-(4-thiomorpholin-4-ylmethyl-phenyl)-methanone, and (4-cyclopropyl-piperazin-1-yl)-[4-(2-hydroxymethyl-morpholin-4-ylmethyl)-phenyl]-methanone, and enantiomers, hydrates, solvates, and pharmaceutically acceptable salts thereof.

In particular embodiments, the compound is (4-cyclopropyl-piperazin-1-yl)-(4-morpholin-4-ylmethyl-phenyl)-methanone citrate salt dihydrochloride or (4-cyclopropyl-piperazin-1-yl)-(4-morpholin-4-ylmethyl-phenyl)-methanone citrate salt. In further embodiments, the compound is (4-cyclopropyl-piperazin-1-yl)-[4-(4-fluoro-piperidin-1-ylmethyl)-phenyl]-methanone citrate salt, (4-cyclopropyl-piperazin-1-yl)-(4-thiomorpholin-4-ylmethyl-phenyl)-methanone citrate salt, or (4-cyclopropyl-piperazin-1-yl)-[4-(2-hydroxymethyl-morpholin-4-ylmethyl)-phenyl]-methanone citrate salt.

The present invention provides methods of treating or preventing diseases and conditions mediated by histamine $H_3$ receptor activity. The invention also features pharmaceutical compositions containing such compounds and methods of using such compositions in the treatment or prevention of diseases mediated by histamine $H_3$ receptor activity. The present invention also contemplates a method of treating or preventing a disease or condition in which histamine is involved with a combination therapy of compounds of the present invention administered with any of the following: histamine $H_1$ antagonists, histamine $H_2$ antagonists, neurotransmitter re-uptake blockers, selective serotonin re-uptake inhibitors (SSRIs), serotonin-norepinephrine reuptake inhibitors, noradrenergic reuptake inhibitors, non-selective serotonin-, dopamine- or norepinephrine-re-uptake inhibitors, modafinil, and topiramate.

The $pK_a$ of a given compound affects the degree of ionization at physiological pH. As unionized forms are more lipophilic, they can penetrate membranes, including the blood-brain barrier, more readily. Although calculated $pK_a$ values for the a cyclopropyl amine compound of the present invention (Example 1) were similar to that obtained for an isopropyl analog (Comparative Example 1), the measured $pK_a$'s differed greatly. Although it has been suggested that a cyclopropyl amine is approximately ten times less basic than aliphatic amines (Zaragoza, et al. J. Med. Chem. 2004, 47, 2833-2838), no direct experimental evidence has been reported (Love, et al. J. Am. Chem. Soc. 1968, 90 (10), 2455-2462). Therefore, replacement of a cyclopropyl group for an aliphatic one may produce a higher fraction of non-protonated amine at physiological pH and, thus, serve to improve permeability of membranes (Zaragoza, et al. J. Med. Chem. 2005, 48, 306-311). These data indicate that cyclopropyl amines may tend toward a greater permeability and volume of distribution ($V_d$) than aliphatic amines of similar structure.

The present invention provides experimental evidence demonstrating a significant decrease in basicity for Example 1, a cyclopropyl amine, relative to its isopropyl and cyclobutyl amine analogs. However, cyclopropyl amines of the present invention actually showed a pharmacokinetic profile that contrasted with the results predicted in the literature. For example, Example 1B displayed a shorter half-life ($T_{1/2}$) and lower volume of distribution ($V_d$) than Comparative Examples 1B and 2B. Similarly, Example 2B displayed a shorter $T_{1/2}$ and lower $V_d$ than Comparative Examples 3B and 4B; Example 3B displayed a shorter $T_{1/2}$ and lower $V_d$ than Comparative Example 5B, and Example 4B displayed a shorter $T_{1/2}$ and lower $V_d$ than Comparative Example 6B.

Additional features and advantages of the invention will become apparent from the detailed description and examples below, and the appended claims.

DETAILED DESCRIPTION OF THE INVENTION

The invention may be more fully appreciated by reference to the following description, including the following glossary of terms and the concluding examples. For the sake of brevity, the disclosures of the publications cited in this specification are herein incorporated by reference.

As used herein, the terms "including", "containing" and "comprising" are used herein in their open, non-limiting sense.

Isomeric forms of the compounds of the present invention, and of their pharmaceutically acceptable salts, are encompassed within the present invention, and reference herein to one of such isomeric forms is meant to refer to at least one of such isomeric forms. One of ordinary skill in the art will recognize that compounds according to this invention may exist, for example in a single isomeric form whereas other compounds may exist in the form of an isomeric mixture. For example, the present invention encompasses optical isomers of the compounds described herein, including enantiomers and mixtures thereof. In addition, certain compounds referred to herein can exist in solvated or hydrated forms as well as unsolvated forms. It is understood that this invention encompasses all such solvated and unsolvated forms of the compounds of this invention.

Compounds according to the present invention that have been modified to be detectable by some analytic technique are also within the scope of this invention. The compounds of the present invention may be labeled with radioactive elements such as $^{125}I$, $^{18}F$, $^{11}C$, $^{64}Cu$, $^{3}H$, $^{14}C$, and the like for use in imaging or for radioactive treatment of patients. An example of such compounds is an isotopically labeled compound, such as an $^{18}F$ isotopically labeled compound that may be used as a probe in detection and/or imaging techniques, such as positron emission tomography (PET) and single-photon emission computed tomography (SPECT). Preferably, compounds of the present invention labeled with $^{18}F$ or $^{11}C$ may be used as a positron emission tomography (PET) molecular probe for studying histamine-mediated disorders. Alternatively, compounds of the present invention labeled with $^{14}C$ may be used in metabolic studies. Another example of such compounds is an isotopically labeled compound, such as a deuterium and/or tritium labeled compound, that may be used in reaction kinetic studies. The compounds described herein may be reacted with an appropriate functionalized radioactive reagents using conventional chemistry to provide radiolabeled compounds.

The compounds as described above may be made according to processes within the skill of the art and/or that are described in the schemes and examples that follow. To obtain the various compounds herein, starting materials may be employed that carry the ultimately desired substituents though the reaction scheme with or without protection as appropriate. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", $3^{rd}$ ed., John Wiley & Sons, 1999. The protecting groups may be removed at a convenient subsequent stage using methods known from the art. Alternatively, it may be necessary to employ, in the place of the ultimately desired substituent, a suitable group that may be carried through the reaction scheme and replaced as appropriate with the desired substituent. Such compounds, precursors, or prodrugs are also within the scope of the invention. Reactions may be performed between the melting point and the reflux temperature of the solvent, and preferably between 0° C. and the reflux temperature of the solvent.

The compounds as described above may be made according to Schemes A-C below. Persons skilled in the art will recognize that certain compounds are more advantageously produced by one scheme as compared to the other. In addition, synthetic sequences described in U.S. patent application Ser. No. 10/690,115 are hereby incorporated by reference and may be applied to the preparation of compounds of the present invention. One skilled in the art will recognize that compounds of Formula (I) where $R^1R^2N-$ is morpholinyl, 4-fluoropiperidinyl, thiomorpholinyl, or 2-hydroxymethyl-morpholin-4-yl are compounds of the present invention.

droxybenzotriazole (HOBt). Preferably, reactions are run with EDC/HOBt in the presence of 4-(dimethylamino)pyridine (DMAP), in a solvent such as $CH_2Cl_2$. Benzaldehydes of formula (XII) may then be reacted with suitable amines $R^1NR^2H$ (where $R^1NR^2H$ is morpholine, 4-fluoropiperidine, thiomorpholine, or morpholin-2-yl-methanol) under reductive amination conditions to provide benzyl amines (XIII). Suitable reducing agents include $NaCNBH_3$ or $NaB(OAc)_3H$ in a solvent such as methanol or dichloroethane. Preferred conditions include $NaB(OAc)_3H$ in methanol. The protecting group "PG" may then be removed under standard deprotection conditions to provide amines of formula (XIV). Where PG is Boc, deprotection may be effected using HCl in 1,4-dioxane or trifluoroacetic acid (TFA) in $CH_2Cl_2$. Amines (XV) are converted to the corresponding cyclopropyl amines of Formula (I) through reaction with [(1-methoxycyclopropyl)oxy]trimethylsilane or [(1-ethoxycyclopropyl)oxy]-trimethylsilane (R is methyl or ethyl) under conditions similar to those described in J. Med. Chem. 2004, 47 (11), 2733-2738 and Tetrahedron Lett. 1995, 36 (41), 7399-7402.

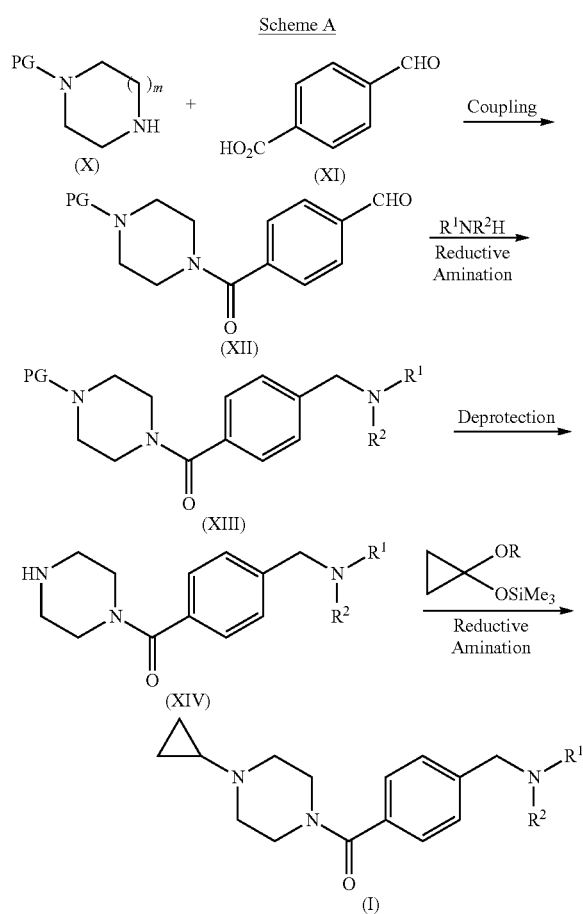

Scheme A

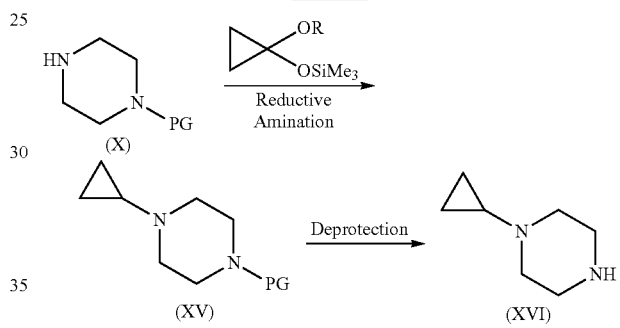

Scheme B

Alternatively, compounds of the present invention may be prepared as in Schemes B and C. To this end, protected heterocycle (X), where PG is as defined previously, may be reacted with [(1-methoxycyclopropyl)oxy]-trimethylsilane or [(1-ethoxycyclopropyl)oxy]trimethylsilane as described in J. Med. Chem. 2004, 47 (11), 2733-2738 and Tetrahedron Lett. 1995, 36 (41), 7399-7402. Preferably, PG is a Boc group. The group "PG" may then be removed under standard deprotection conditions to provide cyclopropyl amines of formula (XVI). Where PG is Boc, preferred conditions include a mixture of HCl in a solvent such as 1,4-dioxane.

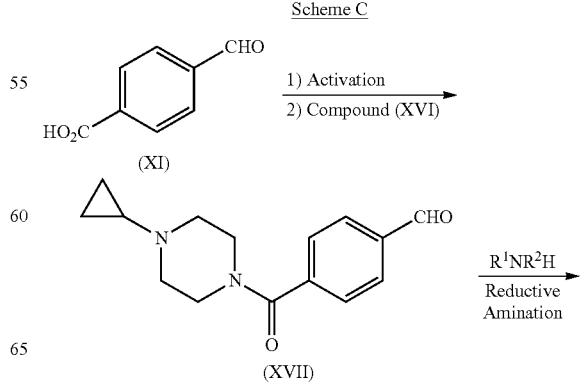

Scheme C

Referring to Scheme A, amines of formula (X), where PG is cyclopropyl or a suitable protecting group such as a benzyl or tert-butylcarbamoyl (Boc), may be coupled with benzoic acids of formula (XI), either through activation of the acid to the acid chloride or acid fluoride followed by reaction with the amine, or directly under peptide coupling conditions, such as 1,1'-carbonyldiimidazole (CDI) or 1-(3-dimethylaminopropyl)-3-ethylcarbodiimide hydrochloride (EDC)/1-hy-

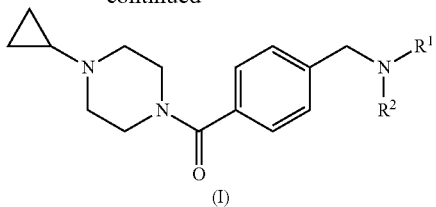

(I)

Acids of formula (XI) may be coupled (through activation or directly as described in Scheme A) with amines (XVI) to form amides (XVII). Reductive amination with a suitable amine as described in Scheme A gives rise to compounds of Formula (I).

Compounds of the present invention may be converted to their corresponding salts using methods known to those skilled in the art. For example, free base forms of compounds of the present invention may be treated with TFA, HCl, or citric acid in a solvent such as methanol (MeOH) or ethanol (EtOH) to provide the corresponding salt forms.

Compounds prepared according to the schemes described above may be obtained as single enantiomers or diastereomers, or as racemic mixtures or mixtures of enantiomers or diastereomers. Where such mixtures are obtained, isomers may be separated using conventional methods such as chromatography or crystallization. Where racemic (1:1) and non-racemic (not 1:1) mixtures of enantiomers are obtained, single enantiomers may be isolated using conventional separation methods known to one skilled in the art. Particularly useful separation methods may include chiral chromatography, recrystallization, resolution, diastereomeric salt formation, or derivatization into diastereomeric adducts followed by separation.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with a compound of the present invention or with a compound that converts to a compound of the present invention in vivo after administration to the patient. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

For therapeutic use, salts of the compounds of the present invention are those that are pharmaceutically acceptable. However, salts of acids and bases that are non-pharmaceutically acceptable may also find use, for example, in the preparation or purification of a pharmaceutically acceptable compound. All salts, whether pharmaceutically acceptable or not, are included within the ambit of the present invention.

Pharmaceutically acceptable salts of compounds according to the present invention refer to those salt forms of the compounds of the present invention which would be apparent to the pharmaceutical chemist, i.e., those that are non-toxic and that would favorably affect the pharmacokinetic properties of said compounds of the present invention, such as sufficient palatability, absorption, distribution, metabolism and excretion. Other factors, more practical in nature, which are also important in the selection, are cost of raw materials, ease of crystallization, yield, stability, hygroscopicity and flowability of the resulting bulk drug.

Examples of acids that may be used in the preparation of pharmaceutically acceptable salts include the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Compounds of the present invention containing acidic protons may be converted into their therapeutically active non-toxic metal or amine addition salt forms by treatment with appropriate organic and inorganic bases. Appropriate base salt forms comprise, for example, the ammonium salts; the alkali and earth alkaline metal salts (e.g. lithium, sodium, potassium, magnesium, calcium salts, which may be prepared by treatment with, for example, magnesium hydroxide, calcium hydroxide, potassium hydroxide, zinc hydroxide, or sodium hydroxide); and amine salts made with organic bases (e.g. primary, secondary and tertiary aliphatic and aromatic amines such as L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine). See, e.g., S. M. Berge, et al., "Pharmaceutical Salts", J. Pharm. Sci., 1977, 66:1-19, and *Handbook of Pharmaceutical Salts, Properties, Selection, and Use*; Stahl, P. H., Wermuth, C. G., Eds.; Wiley-VCH and VHCA: Zurich, 2002, which are incorporated herein by reference.

The compounds of the present invention are modulators of the histamine $H_3$ receptor, and as such, the compounds are useful in the treatment of disease states mediated by histamine $H_3$ receptor activity. Thus, the compounds of the present invention may be used in a method of treating a subject suffering from or diagnosed with a disease mediated by histamine $H_3$ receptor activity, comprising administering to a subject in need of such treatment an effective amount of a compound of the present invention, or a pharmaceutically acceptable salt thereof. Particularly, the compounds may be used in methods for treating or preventing neurologic or neuropsychiatric disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy with or without associated cataplexy, disorders of sleep/wake homeostasis, idiopathic somnolence, excessive daytime sleepiness (EDS), circadian rhythm disorders, sleep/fatigue disorders, fatigue, drowsiness associated with sleep apnea, sleep impairment due to perimenopausal hormonal shifts, Parkinson's-related fatigue, MS-related fatigue, depression-related fatigue, chemotherapy-induced fatigue, eating disorders, obesity, motion sickness, vertigo, schizophrenia, substance abuse, bipolar disorders, manic disorders and depression, as well as other disorders in which the histamine $H_3$ receptor is involved, such as upper airway allergic response, asthma, itch, nasal congestion and allergic rhinitis in a subject in need thereof. For example, the invention features methods for preventing, inhibiting the progression of, or treating upper airway allergic response, asthma, itch, nasal congestion and allergic rhinitis. Excessive daytime sleepiness (EDS) may occur with or without associated sleep apnea, shift work, fibromyalgia, MS, and the like.

The compounds of the present invention may be used in methods for treating or preventing disease states selected from the group consisting of: cognitive disorders, sleep disorders, psychiatric disorders, and other disorders.

Cognitive disorders include, for example, dementia, Alzheimer's disease (Panula, P. et al., Soc. Neurosci. Abstr. 1995, 21, 1977), cognitive dysfunction, mild cognitive impairment (pre-dementia), attention deficit hyperactivity disorders (ADHD), attention-deficit disorders, and learning and memory disorders (Barnes, J. C. et al., Soc. Neurosci. Abstr. 1993, 19, 1813). Learning and memory disorders include, for example, learning impairment, memory impairment, age-related cognitive decline, and memory loss. $H_3$ antagonists have been shown to improve memory in a variety of memory tests, including the elevated plus maze in mice (Miyazaki, S. et al. *Life Sci.* 1995, 57 (23), 2137-2144), a two-trial place recognition task (Orsetti, M. et al. *Behav. Brain Res.* 2001, 124 (2), 235-242), the passive avoidance test in mice (Miyazaki, S. et al. *Meth. Find. Exp. Clin. Pharmacol.* 1995, 17 (10), 653-658) and the radial maze in rats (Chen, Z. *Acta Pharmacol. Sin.* 2000, 21 (10), 905-910). Also, in the spontaneously hypertensive rat, an animal model for the learning impairments in attention-deficit disorders, $H_3$ antagonists were shown to improve memory (Fox, G. B. et al. *Behav. Brain Res.* 2002, 131 (1-2), 151-161).

Sleep disorders include, for example, insomnia, disturbed sleep, narcolepsy (with or without associated cataplexy), cataplexy, disorders of sleep/wake homeostasis, idiopathic somnolence, excessive daytime sleepiness (EDS), circadian rhythm disorders, fatigue, lethargy, REM-behavioral disorder, and jet lag. Fatigue and/or sleep impairment may be caused by or associated with various sources, such as, for example, sleep apnea, perimenopausal hormonal shifts, Parkinson's disease, multiple sclerosis (MS), depression, chemotherapy, or shift work schedules.

Psychiatric disorders include, for example, schizophrenia (Schlicker, E. and Marr, I., Naunyn-Schmiedeberg's Arch. Pharmacol. 1996, 353, 290-294), bipolar disorders, manic disorders, depression (Lamberti, C. et al. *Br. J. Pharmacol.* 1998, 123 (7), 1331-1336; Perez-Garcia, C. et al. *Psychopharmacology* 1999, 142 (2), 215-220) (Also see: Stark, H. et al., Drugs Future 1996, 21 (5), 507-520; and Leurs, R. et al., Prog. Drug Res. 1995, 45, 107-165 and references cited therein.), obsessive-compulsive disorder, and post-traumatic stress disorder.

Other disorders include, for example, motion sickness, vertigo (including vertigo and benign postural vertigo), tinitus, epilepsy (Yokoyama, H. et al., Eur. J. Pharmacol. 1993, 234, 129-133), migraine, neurogenic inflammation, eating disorders (Machidori, H. et al., Brain Res. 1992, 590, 180-186), obesity, substance abuse disorders, movement disorders (e.g. restless leg syndrome), and eye-related disorders (e.g. macular degeneration and retinitis pigmentosis).

Said methods of treating and preventing comprise the step of administering to a mammal suffering therefrom an effective amount of at least one compound of the present invention.

The present invention also contemplates a method of treating or preventing a histamine-mediated disease or condition with a combination therapy for the treatment of allergic rhinitis, nasal congestion, and allergic congestion, comprising: a) administering an effective amount of at least one compound of the present invention, and b) administering an effective amount of one or more histamine $H_1$ or $H_2$ antagonists. Suitable histamine $H_1$ antagonists include: loratidine (CLARITIN™), desloratidine (CLARINEX™), fexofenadine (ALLEGRA™) and cetirizine (ZYRTECT™).

The present invention also contemplates a method of treating or preventing a histamine-mediated disease or condition with a combination therapy for the treatment of depression, mood disorders or schizophrenia, comprising: a) administering an effective amount of at least one compound of the present invention, and b) administering an effective amount of one or more neurotransmitter re-uptake blockers. Suitable neurotransmitter re-uptake blockers include: selective serotonin re-uptake inhibitors (SSRIs), serotonin-norepinephrine reuptake inhibitors, noradrenergic reuptake inhibitors, or non-selective serotonin-, dopamine- or norepinephrine re-uptake inhibitors. Particular examples of neurotransmitter re-uptake blockers include fluoxetine (PROZAC™), sertraline (ZOLOFT™), paroxetine (PAXIL™), and amitryptyline.

The present invention also contemplates a method of treating or preventing a histamine-mediated disease or condition with a combination therapy for the treatment of narcolepsy, excessive daytime sleepiness (EDS), Alzheimer's disease, depression, attention deficit disorders, MS-related fatigue, post-anesthesia grogginess, cognitive impairment, schizophrenia, spasticity associated with cerebral palsy, age-related memory decline, idiopathic somnolence, or jet-lag, comprising: a) administering an effective amount of at least one compound of the present invention, and b) administering an effective amount of modafinil.

In another embodiment, the present invention contemplates a method of treating or preventing a histamine-mediated disease or condition with a combination therapy comprising: a) administering an effective amount of at least one compound of the present invention, and b) administering an effective amount of topiramate (Topamax). In particular, such methods are useful for the treatment of obesity. Preferably, the combination method employs doses of topiramate in the range of about 20 to 300 mg per dose.

Compounds of the present invention may be administered in pharmaceutical compositions to treat patients (humans and other mammals) with disorders mediated by the $H_3$ receptor. Thus, the invention features pharmaceutical compositions containing at least one compound of the present invention and a pharmaceutically acceptable carrier. A composition of the invention may further include at least one other therapeutic agent such as $H_1$ antagonists, SSRIs, topiramate, or modafinil (for example, a combination formulation or combination of differently formulated active agents for use in a combination therapy method).

The present invention also features methods of using or preparing or formulating such pharmaceutical compositions. The pharmaceutical compositions can be prepared using conventional pharmaceutical excipients and compounding techniques known to those skilled in the art of preparing dosage forms. It is anticipated that the compounds of the invention can be administered by oral, parenteral, rectal, topical, or ocular routes, or by inhalation. Preparations may also be designed to give slow release of the active ingredient. The preparation may be in the form of tablets, capsules, sachets, vials, powders, granules, lozenges, powders for reconstitution, liquid preparations, or suppositories. Preferably, compounds may be administered by intravenous infusion or topical administration, but more preferably by oral administration.

For oral administration, the compounds of the invention can be provided in the form of tablets or capsules, or as a solution, emulsion, or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert fillers include sodium and calcium carbonate, sodium and calcium phosphate, lactose, starch, sugar, glucose, methyl cellulose, magnesium stearate, mannitol, sorbitol, and the like; typical liquid oral excipients include ethanol, glycerol, water and the like. Starch, polyvinyl-pyrrolidone, sodium starch glycolate, microcrystalline cellulose, and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate to delay absorption in the gastrointestinal tract, or may be coated with an enteric coating. Capsules for oral use include hard gelatin capsules in which the active ingredient is mixed with a solid, semi-solid, or liquid diluent, and soft gelatin capsules wherein the active ingredient is mixed with water, an oil such as peanut oil or olive oil, liquid paraffin, a mixture of mono and di-glycerides of short chain fatty acids, polyethylene glycol 400, or propylene glycol.

Liquids for oral administration may be suspensions, solutions, emulsions or syrups or may be presented as a dry product for reconstitution with water or other suitable vehicles before use. Compositions of such liquid may contain pharmaceutically-acceptable excipients such as suspending agents (for example, sorbitol, methyl cellulose, sodium alginate, gelatin, hydroxyethylcellulose, carboxymethylcellulose, aluminium stearate gel and the like); non-aqueous vehicles, which include oils (for example, almond oil or fractionated coconut oil), propylene glycol, ethyl alcohol or water; preservatives (for example, methyl or propyl p-hydroxybenzoate or sorbic acid); wetting agents such as lecithin; and, if needed, flavoring or coloring agents.

The compounds of this invention may also be administered by non-oral routes. The compositions may be formulated for rectal administration as a suppository. For parenteral use, including intravenous, intramuscular, intraperitoneal, or subcutaneous routes, the compounds of the invention will generally be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit dose form such as ampules or disposable injection devices, in multi-dose forms such as vials from which the appropriate dose may be withdrawn, or in a solid form or pre-concentrate that can be used to prepare an injectable formulation. Another mode of administration of the compounds of the invention may utilize a patch formulation to affect transdermal delivery. The compounds of this invention may also be administered by inhalation, via the nasal or oral routes using a spray formulation consisting of the compound of the invention and a suitable carrier.

Methods are known in the art for determining effective doses for therapeutic (treatment) and prophylactic (preventative) purposes for the pharmaceutical compositions or the drug combinations of the present invention, whether or not formulated in the same composition. The specific dosage level required for any particular patient will depend on a number of factors, including severity of the condition being treated, the route of administration, metabolic rate, and the weight of the patient. For therapeutic purposes, "effective dose" or "effective amount" refers to that amount of each active compound or pharmaceutical agent, alone or in combination, that elicits the biological or medicinal response in a tissue system, animal, or human that is being sought by a researcher, veterinarian, medical doctor, or other clinician, which includes alleviation of the symptoms of the disease or disorder being treated. For prophylactic purposes (i.e., preventing or inhibiting the onset or progression of a disorder), the term "effective dose" or "effective amount" refers to that amount of each active compound or pharmaceutical agent, alone or in combination, that inhibits in a subject the onset or progression of a disorder as being sought by a researcher, veterinarian, medical doctor, or other clinician, the delaying of which disorder is mediated, at least in part, by the modulation of the histamine $H_3$ receptor. Methods of combination therapy include co-administration of a single formulation containing all active agents; essentially contemporaneous administration of more than one formulation; and administration of two or more active agents separately formulated.

It is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg.

Preferably, oral doses range from about 0.05 to 200 mg/kg, daily, taken in 1 to 4 separate doses. Some compounds of the invention may be orally dosed in the range of about 0.05 to about 50 mg/kg daily, others may be dosed at 0.05 to about 20 mg/kg daily, while still others may be dosed at 0.1 to about 10 mg/kg daily. Infusion doses can range from about 1 to 1000 µg/kg/min of inhibitor, admixed with a pharmaceutical carrier over a period ranging from several minutes to several days. For topical administration compounds of the present invention may be mixed with a pharmaceutical carrier at a concentration of about 0.1% to about 10% of drug to vehicle.

EXAMPLES

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention.

Chemical Examples and Data

Mass spectra were obtained on an Agilent series 1100 MSD using electrospray ionization (ESI) in either positive or negative modes as indicated. Nuclear magnetic resonance (NMR) spectra were obtained on a Bruker model DPX400 (400 MHz), DPX500 (500 MHz), or DPX600 (600 MHz) spectrometer. The format of the $^1$H NMR data below is: chemical shift in ppm down field of the tetramethylsilane reference (multiplicity, coupling constant J in Hz, integration).

Reversed-phase high-pressure liquid chromatography (HPLC) was performed on a Hewlett Packard HPLC, Zorbax Eclipse XDB-C8, 5 μm, 4.6×150 mm column, with a gradient of 1 to 99% acetonitrile/water/0.05% TFA over 8 min.

Chemical names were generated using ChemDraw Ultra 6.0.2 (CambridgeSoft Corp., Cambridge, Mass.).

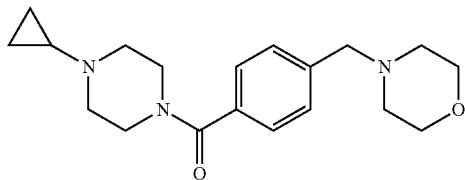

Example 1

(4-Cyclopropyl-piperazin-1-yl)-(4-morpholin-4-ylmethyl-phenyl)-methanone

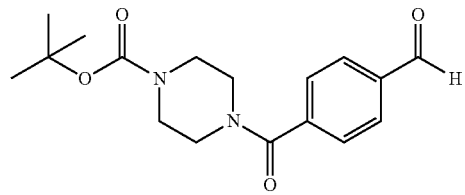

Step A. 4-(4-Formyl-benzoyl)-piperazine-1-carboxylic acid tert-butyl ester. A suspension of 4-carboxybenzaldehyde (3.10 g) in CH$_2$Cl$_2$ was treated sequentially with piperazine-1-carboxylic acid tert-butyl ester (3.6 g), EDC (3.86 g), HOBt (2.68 g), and DMAP (0.020 g). After 18 h, the mixture was extracted with 1 N NaOH and then with 1 N HCl. The organic layer was dried (Na$_2$SO$_4$) and concentrated to give the title compound (5.11 g, 78%). MS (ESI): mass calcd. for C$_{17}$H$_{22}$N$_2$O$_4$, 318.16; m/z found, 219.3 [(M−100)+H]$^+$. $^1$H NMR (CDCl$_3$): 10.04 (s, 1H), 7.93 (d, J=8.2, 2H), 7.54 (d, J=8.1, 2H), 3.82-3.67 (m, 2H), 3.58-3.30 (m, 6H), 1.46 (s, 9H).

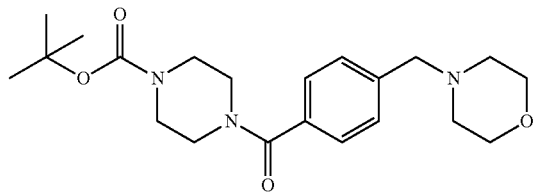

Step B. 4-(4-Morpholin-4-ylmethyl-benzoyl)-piperazine-1-carboxylic acid tert-butyl ester. A solution of 4-(4-formyl-benzoyl)piperazine-1-carboxylic acid tert-butyl ester (2.06 g) in methanol (100 mL) was treated with morpholine (4 mL) and NaB(OAc)$_3$H (6.98 g, in portions over 1 h). After 3 h, the mixture was diluted with satd. aq. NaHCO$_3$ and extracted with CH$_2$Cl$_2$. The organic layer was dried (Na$_2$SO$_4$) and concentrated. The residue was purified by column chromatography (SiO$_2$) to give the title compound (1.22 g, 48%). MS (ESI): mass calcd. for C$_{21}$H$_{31}$N$_3$O$_4$, 389.23; m/z found, 390.4 [M+H]$^+$. $^1$H NMR (CDCl$_3$): 7.39-7.33 (m, 4H), 3.75-3.66 (m, 6H), 3.50 (s, 2H), 3.51-3.33 (m, 6H), 2.45-2.41 (m, 4H), 1.46 (s, 9H).

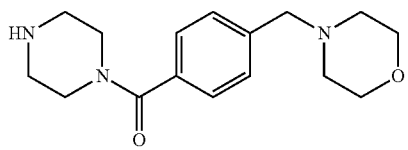

Step C. (4-Morpholin-4-ylmethyl-phenyl)-piperazin-1-yl-methanone. A solution of 4-(4-morpholin-4-ylmethyl-benzoyl)-piperazine-1-carboxylic acid tert-butyl ester (1.163 g) in CH$_2$Cl$_2$ (10 mL) was treated with TFA (~4 mL). After 30 min, additional TFA (5 mL) was added, and the mixture was stirred for a further 2 h. The mixture was diluted with diluted with satd. aq. NaHCO$_3$ and extracted with CH$_2$Cl$_2$. The organic layer was dried (Na$_2$SO$_4$) and concentrated. The residue was purified by column chromatography (SiO$_2$) to give the title compound (0.255 g, 30%). MS (ESI): mass calcd. for C$_{16}$H$_{23}$N$_3$O$_2$, 289.18; m/z found, 290.4 [M+H]$^+$. $^1$H NMR (CDCl$_3$): 7.41-7.35 (m, 4H), 3.95-3.70 (m, 6H), 3.52 (s, 2H), 3.09-2.80 (m, 6H), 2.49-2.42 (m, 4H).

Step D. A solution of (4-morpholin-4-ylmethyl-phenyl)-piperazin-1-yl-methanone (0.128 g) in methanol (7.5 mL) was treated with (1-ethoxy-cyclopropoxy)-trimethyl-silane (1.5 mL), acetic acid (0.2 mL), and NaBH$_3$CN (~400 mg). The mixture was heated at 60° C. for 18 h, and then was cooled to rt and concentrated. The residue was diluted with 1 N NaOH and extracted with CH$_2$Cl$_2$. The organic layer was dried (Na$_2$SO$_4$) and concentrated. The residue was purified by column chromatography (SiO$_2$) to give the title compound (0.0548 g, 38%). MS (ESI): mass calcd. for C$_{19}$H$_{27}$N$_3$O$_2$, 329.21; m/z found, 330.4 [M+H]$^+$. $^1$H NMR (CDCl$_3$): 7.36 (s, 4H), 3.79-3.68 (m, 6H), 3.50 (s, 2H), 3.44-3.32 (m, 2H), 2.74-2.61 (m, 2H), 2.60-2.50 (s, 2H), 2.45-2.40 (m, 4H), 1.66-1.62 (m, 1H), 0.49-0.44 (m, 2H), 0.44-0.39 (m, 2H).

Alternative Preparation of Example 1.

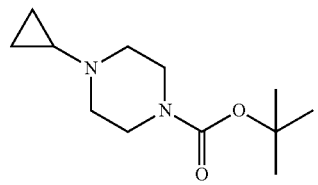

Step A. tert-Butyl 4-cyclopropylpiperazine-1-carboxylate. A mixture of tert-butyl piperazine-1-carboxylate (75.0 g), tetrahydrofuran (THF) (500 mL), methanol (500 mL), [(1-ethoxycyclopropyl)oxy]trimethylsilane (161 mL), NaBH$_3$CN (38.0 g), and acetic acid (37 mL) was heated at 60° C. for 5 h. The mixture was cooled to rt, treated with water (30 mL) and stirred for 5 min. The mixture was then treated with 1 N NaOH (130 mL) and was further stirred for 15 min. The mixture was concentrated, and the remaining aqueous solution was extracted with CH$_2$Cl$_2$ (500 mL). The organic layer was washed with 1 N NaOH (500 mL). The combined aqueous layers were extracted with CH$_2$Cl$_2$ (150 mL). The combined organic layers were washed with brine (400 mL), dried (Na$_2$SO$_4$), and concentrated to give the title compound as a white solid (92 g, 100%). MS (ESI): mass calcd. for C$_{12}$H$_{22}$N$_2$O$_2$, 226.17; m/z found, 227.2 [M+H$^+$]. $^1$H NMR (400 MHz, CDCl$_3$): 3.39 (t, J=5.0 Hz, 4H), 2.55 (t, J=4.9 Hz, 4H), 1.60 (ddd, J=10.3, 6.5, 3.8 Hz, 1H), 1.46 (s, 9H), 0.49-0.38 (m, 4H).

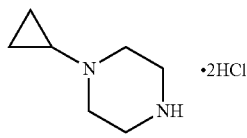

Step B. 1-Cyclopropylpiperazine dihydrochloride. A solution of tert-butyl 4-cyclopropylpiperazine-1-carboxylate (92 g) in 1,4-dioxane (200 mL) was treated with HCl (4 M in 1,4-dioxane, 500 mL) over 10 min while maintaining the temperature below 40° C. After the addition was complete, the mixture was heated at 45° C. for 9 h and then was cooled to rt. The thick suspension was diluted with hexanes (400 mL) and was cooled to 10° C. The resulting solid was collected by filtration, washed with hexanes, and dried to give the title compound as a white solid (78 g, 96%). MS (ESI): mass calcd. for C$_7$H$_{14}$N$_2$, 126.12; m/z found, 127.0 [M+H$^+$]. $^1$H NMR (400 MHz, D$_2$O): 3.65 (br t, J=4.7 Hz, 4H), 3.47 (br t, J=5.5 Hz, 4H), 2.85 (br quintet, J=5.8 Hz, 1H), 0.94 (br s, 2H), 0.92 (br s, 2H).

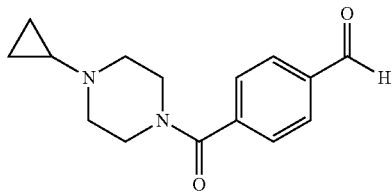

Step C. 4-(4-Cyclopropyl-piperazine-1-carbonyl)-benzaldehyde. A mixture of 4-formyl-benzoic acid (54.4 g), toluene (500 mL), N,N-dimethylformamide (DMF) (3.6 mL), and thionyl chloride (30.4 mL) was heated at 60° C. for 2 h and then was cooled to 5° C. In a separate flask, a 5° C. mixture of NaOH (50.7 g), water (550 mL), and toluene (150 mL) was treated with 1-cyclopropyl-piperazine dihydrochloride (70.0 g) in portions while the temperature was maintained below 10° C. After the addition was complete, the mixture was cooled to 5° C. and treated with the crude acyl chloride solution prepared as above at a rate such that the temperature did not exceed 10° C. After the addition was complete, the mixture was allowed to warm to rt and was stirred overnight. The biphasic mixture was basified to pH ~10 with 1 N NaOH (300 mL). The layers were separated and the aqueous layer was extracted with toluene (100 mL×2). The combined organic layers were washed with brine (200 mL), dried (Na$_2$SO$_4$), and concentrated to give the title compound as pale yellow viscous oil (56.0 g, 62%). HPLC: R$_T$=5.19 min. MS (ESI): mass calcd. for C$_{15}$H$_{18}$N$_2$O$_2$, 258.14; m/z found, 258.9 [M+H$^+$]. $^1$H NMR (400 MHz, CDCl$_3$): 10.1 (s, 1H), 7.94 (pseudo d, J=8.2 Hz, 2H), 7.56 (pseudo d, J=8.1 Hz, 2H), 3.77 (br s, 2H), 3.33 (br s, 2H), 2.71 (br s, 2H), 2.55 (br s, 2H), 1.66 (ddd, J=10.2, 6.6, 3.7 Hz, 1H), 0.52-0.46 (m, 2H), 0.45-0.40 (br s, 2H).

Step D. (4-Cyclopropyl-piperazin-1-yl)-(4-morpholin-4-ylmethyl-phenyl)-methanone. To a solution of 4-(4-cyclopropyl-piperazine-1-carbonyl)-benzaldehyde (56.0 g) in 1,2-dichloroethane (550 mL) was added morpholine (37.8 mL) dropwise over 5 min. The mixture was cooled to 10° C. and was treated with NaB(OAc)$_3$H (64.3 g) in portions over 1 h. After a further 2 h, the mixture was warmed to rt, and a water bath was used to keep the temperature below 20° C. After 18 h, water (60 mL) was added while the temperature was kept under 20° C. by the addition of small amounts of ice. After 20 min, the mixture was basified to pH ~10 with 1 N NaOH (450 mL) and the mixture was stirred for 10 min. The layers were separated, and the organic layer was washed with 1 N NaOH (150 mL). The combined aqueous layers were extracted with CH$_2$Cl$_2$ (200 mL). The combined organic layers were washed with brine (200 mL), dried (Na$_2$SO$_4$), and concentrated to give the title compound as pale yellow viscous oil (68.0 g, 95%). HPLC: R$_T$=4.39 min. MS (ESI): mass calcd. for C$_{19}$H$_{27}$N$_3$O$_2$, 329.21; m/z found, 330.2 [M+H$^+$]. $^1$H NMR (400 MHz, CDCl$_3$): 7.35 (br s, 4H), 3.73 (br s, 2H), 3.69 (t, J=4.6 Hz, 4H), 3.50 (s, 2H), 3.37 (br s, 2H), 2.67 (br s, 2H), 2.53 (br s, 2H), 2.43 (t, J=4.2 Hz, 4H), 1.63 (ddd, J=10.3, 6.7, 3.7 Hz, 1H), 0.49-0.43 (m, 2H), 0.42-0.39 (br s, 2H). $^{13}$C NMR (101 MHz, CDCl$_3$): 170.6, 140.0, 135.1, 129.5, 127.5, 67.4, 63.4, 54.0, 38.7, 6.3.

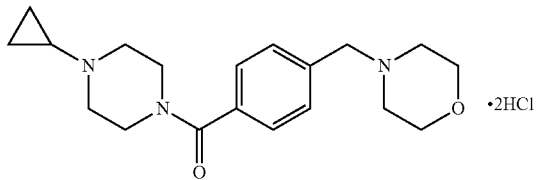

Example 1A (4-Cyclopropyl-piperazin-1-yl)-(4-morpholin-4-ylmethyl-phenyl)-methanone dihydrochloride A solution of (4-cyclopropyl-piperazin-1-yl)-(4-morpholin-4-ylmethyl-phenyl)-methanone (68.0 g) in ethanol (400 mL) was heated to 60° C. and treated with conc. HCl (37.8 mL) dropwise over 40 min. A precipitate started to form after ~20 mL of HCl had been added. After the addition was complete, the thick suspension was slowly cooled to 20° C. over 3 h. The solid was collected by filtration, washed with ethanol, and dried at 50° C. overnight in a vacuum oven to provide the title compound as a white solid (56.2 g, 68%). HPLC: R$_T$=4.30 min. MS (ESI): mass calcd. for C$_{19}$H$_{27}$N$_3$O$_2$, 329.21; m/z found, 330.0 [M+H$^+$]. $^1$H NMR (400 MHz, D$_2$O): 7.64 (pseudo d, J=8.3 Hz, 2H), 7.58 (pseudo d, J=8.3 Hz, 2H), 4.44 (br s, 2H), 4.20-3.10 (m, 16H), 2.88 (ddd, J=11.2, 6.6, 4.8 Hz, 1H), 1.03-0.98 (m, 4H). $^{13}$C NMR (101 MHz, D$_2$O): 172.1, 135.3, 132.2, 130.9, 128.0, 64.0, 60.5, 52.6, 52.4, 51.7, 44.8, 39.7, 39.5, 3.9.

Example 1B (4-Cyclopropyl-piperazin-1-yl)-(4-morpholin-4-ylmethyl-phenyl)-methanone citrate salt A mixture of (4-cyclopropyl-piperazin-1-yl)-(4-morpholin-4-ylmethyl-phenyl)-methanone (0.476 g, 1.45 mmol) and citric acid (0.281 g, 1.46 mmol) was diluted with methanol (~10 mL). The mixture was heated until homogeneous and then concentrated. The resulting oil was triturated with ethyl acetate and the solid material that formed was dried under vacuum to yield the citrate salt (0.760 g).

The compounds in Examples 2-4 were prepared using methods analogous to those described in the preceding examples, with the appropriate substituent changes.

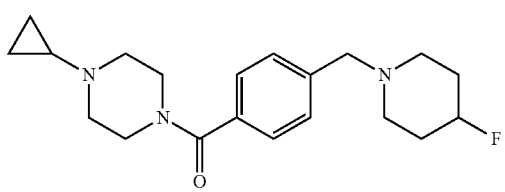

Example 2

(4-Cyclopropyl-piperazin-1-yl)-[4-(4-fluoro-piperidin-1-ylmethyl)-phenyl]-methanone MS (ESI): mass calcd. for $C_{20}H_{28}FN_3O$, 345.22; m/z found, 346.4 [M+H$^+$]. $^1$H NMR (400 MHz, CDCl$_3$): 7.39-7.33 (m, 4H), 4.78-4.58 (m, 1H), 3.82-3.66 (m, 2H), 3.51 (s, 2H), 3.46-3.33 (m, 2H), 2.77-2.49 (m, 6H), 2.43-2.32 (m, 2H), 1.97-1.82 (m, 4H), 1.68-1.63 (m, 1H), 0.52-0.38 (m, 4H).

Example 2B (4-Cyclopropyl-piperazin-1-yl)-[4-(4-fluoro-piperidin-1-ylmethyl)-phenyl]-methanone citrate salt

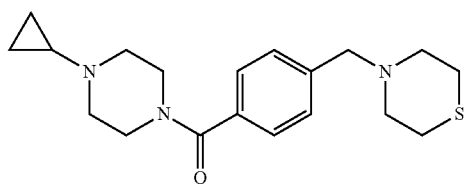

Example 3

(4-Cyclopropyl-piperazin-1-yl)-(4-thiomorpholin-4-ylmethyl-phenyl)-methanone

MS (ESI): mass calcd. for $C_{19}H_{27}N_3OS$, 345.19; m/z found, 346 [M+H$^+$]. $^1$H NMR (400 MHz, CDCl$_3$): 7.37-7.32 (m, 4H), 3.86-3.60 (bm, 2H), 3.53 (s, 2H), 3.53-3.25 (bm, 2H), 2.75-2.61 (bm, 10H), 2.61-2.45 (bm, 2H), 1.66-1.60 (m, 1H), 0.51-0.44 (m, 2H), 0.44-0.38 (m, 6H).

Example 3B (4-Cyclopropyl-piperazin-1-yl)-(4-thiomorpholin-4-ylmethyl-phenyl)-methanone citrate salt

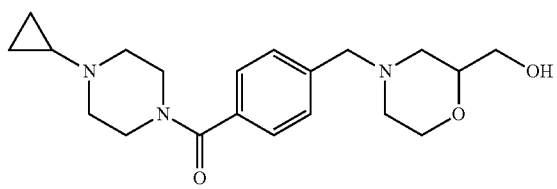

Example 4

(4-Cyclopropyl-piperazin-1-yl)-[4-(2-hydroxymethyl-morpholin-4-ylmethyl)-phenyl]-methanone MS (ESI): mass calcd. for $C_{20}H_{29}N_3O_3$, 359.22; m/z found, 360 [M+H$^+$]. $^1$H NMR (400 MHz, CDCl$_3$): 7.39-7.34 (m, 4H), 3.93-3.87 (m, 1H), 3.85-3.25 (m, 10H), 2.75-2.45 (bm, 6H), 2.25-2.15 (m, 1H), 2.05-1.93 (m, 2H), 1.67-1.60 (m, 1H), 0.52-0.45 (m, 2H), 0.45-0.40 (m, 2H).

Example 4B (4-Cyclopropyl-piperazin-1yl)-[4-(2-hydroxymethyl-morpholin-4-ylmethyl)-phenyl]-methanone citrate salt

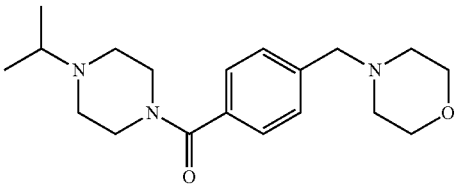

Comparative Example 1

(4-Isopropyl-piperazin-1-yl)-(4-morpholin-4-ylmethyl-phenyl)-methanone

Preparation and analytical data for the title compound was presented in U.S. patent application Ser. No. 10/690,115 (Oct. 21, 2003). The corresponding salt forms were prepared as described for Examples 1A and 1B.

Comparative Example 1A (4-Isopropyl-piperazin-1-yl)-(4-morpholin-4-ylmethyl-phenyl)-methanone dihydrochloride

Comparative Example 1B (4-Isopropyl-piperazin-1-yl)-(4-morpholin-4-ylmethyl-phenyl)-methanone citrate salt

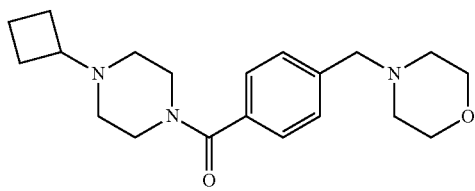

Comparative Example 2

(4-Cyclobutyl-piperazin-1-yl)-(4-morpholin-4-ylmethyl-phenyl)-methanone

The title compound was prepared according to the methods described in Example 1. MS (ESI): mass calcd. for $C_{20}H_{29}N_3O_2$, 343.23; m/z found, 344.4 [M+H$^+$]. $^1$H NMR (400 MHz, CDCl$_3$): 7.39-7.32 (m, 4H), 3.87-3.65 (m, 6H), 3.66-3.36 (m, 4H), 2.80-2.69 (m, 1H), 2.50-2.18 (m, 8H), 2.08-1.99 (m, 2H), 1.93-1.81 (m, 2H), 1.79-1.61 (m, 2H). The corresponding salt forms were prepared as described for Examples 1A and 1B.

Comparative Example 2A (4-Cyclobutyl-piperazin-1-yl)-(4-morpholin-4-ylmethyl-phenyl)-methanone dihydrochloride

Comparative Example 2B (4-Cyclobutyl-piperazin-1-yl)-(4-morpholin-4-ylmethyl-phenyl)-methanone citrate salt The compounds in Comparative Examples 3-6 and their corresponding salt forms were prepared using methods analogous to those described in the preceding examples, with the appropriate substituent changes.

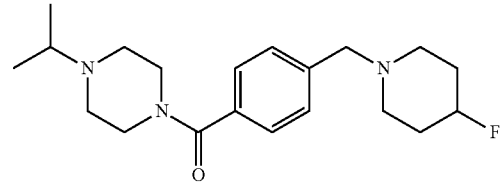

Comparative Example 3

[4-(4-Fluoro-piperidin-1-ylmethyl)-phenyl]-(4-isopropyl-piperazin-1-yl)-methanone MS (ESI): mass calcd. for $C_{20}H_{30}FN_3O$, 347.24; m/z found, 348.4 [M+H$^+$]. $^1$H NMR (400 MHz, CDCl$_3$): 7.36-7.33 (m, 4H), 4.75-4.59 (m, 1H), 3.84-3.71 (m, 2H), 3.50 (s, 2H), 3.49-3.38 (m, 2H), 2.71 (heptet, J=6.6 Hz, 1H), 2.64-2.31 (m, 8H), 1.94-1.82 (m, 4H), 1.04 (d, J=6.3 Hz, 6H).

Comparative Example 3B

[4-(4-Fluoro-piperidin-1-ylmethyl)-phenyl]-(4-isopropyl-piperazin-1-yl)-methanone citrate salt

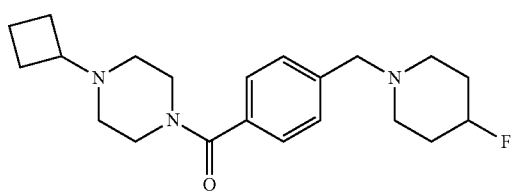

Comparative Example 4

(4-Cyclobutyl-piperazin-1-yl)-[4-(4-fluoro-piperidin-1-ylmethyl)-phenyl]-methanone MS (ESI): mass calcd. for $C_{21}H_{30}FN_3O$, 359.24; m/z found, 360.4 [M+H$^+$]. $^1$H NMR (400 MHz, CDCl$_3$): 7.38-7.34 (m 4H), 4.77-4.60 (m, 1H), 3.88-3.72 (m, 2H), 3.52 (s, 2H), 3.51-3.37 (m, 2H), 2.80-2.71 (m, 1H), 2.63-2.54 (m, 2H), 2.46-2.20 (m, 6H), 2.09-2.01 (m, 2H), 1.97-1.64 (m, 8H).

Comparative Example 4B (4-Cyclobutyl-piperazin-1-yl)-[4-(4-fluoro-piperidin-1-ylmethyl)-phenyl]-methanone citrate salt

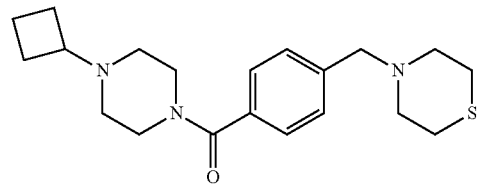

Comparative Example 5

(4-Cyclobutyl-piperazin-1-yl)-(4-thiomorpholin-4-ylmethyl-phenyl)-methanone

MS (ESI): mass calcd. for $C_{20}H_{29}N_3OS$, 359.20; m/z found, 360 [M+H$^+$]. $^1$H NMR (400 MHz, CDCl$_3$): 7.37-7.32 (m, 4H), 3.88-3.65 (bm, 2H), 3.52 (s, 2H), 3.52-3.35 (bm, 2H), 2.80-2.63 (bm, 9H), 2.45-2.28 (bm, 4H), 2.10-1.98 (m, 2H), 1.95-1.79 (m, 2H), 1.78-1.65 (m, 2H).

Comparative Example 5B (4-Cyclobutyl-piperazin-1-yl)-(4-thiomorpholin-4-ylmethyl-phenyl)-methanone citrate salt

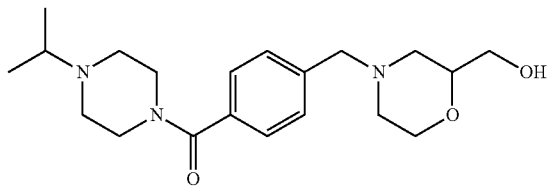

Comparative Example 6

[4-(2-Hydroxymethyl-morpholin-4-ylmethyl)-phenyl]-(4-isopropyl-piperazin-1-yl)-methanone MS (ESI): mass calcd. for $C_{20}H_{31}N_3O_3$, 361.24; m/z found, 362 [M+H$^+$]. $^1$H NMR (400 MHz, CDCl$_3$): 7.38-7.34 (m, 4H), 3.93-3.87 (m, 1H), 3.87-3.35 (m, 10H), 2.73 (heptet, J=6.6 Hz, 1H), 2.70-2.62 (m, 2H), 2.62-2.36 (bm, 4H), 2.24-2.15 (m, 1H), 2.05-1.92 (bm, 2H), 1.05 (d, J=6.5 Hz, 6H).

Comparative Example 6B

[4-(2-Hydroxymethyl-morpholin-4-ylmethyl)-phenyl]-(4-isopropyl-piperazin-1-yl)-methanone citratae salt Physical Chemical Data The measured pK$_a$ values for Example 1, a cyclopropyl amine, was significantly lower than that predicted through calculation (using the Pallas software package from Compu-Drug, Inc.), and also were significantly lower than that observed for Comparative Example 1 (isopropyl amine). Measured pK$_a$, log P, and log D values were determined by pION, Inc. (Woburn, Mass.).

TABLE 1

| | Physical Chemical Data | | | |
|---|---|---|---|---|
| EX | pK$_a$ (calc.) | pK$_a$ (meas.) | log P | log D |
| Ex. 1 | 8.5, 6.2 | 6.5, 5.3 | 0.89 | 0.86 |
| Comp. Ex. 1 | 8.5, 6.2 | 7.6, 6.2 | 0.55 | 0.13 |
| Comp. Ex. 2 | 7.8, 6.2 | 7.4, 6.5 | 2.09 | 1.77 |

Biological Examples and Data

A. Transfection of Cells with Human Histamine Receptor

Cells were grown to about 70% to 80% confluence and removed from the plate with trypsin and pelleted in a clinical centrifuge. The pellet was then re-suspended in 400 µL of complete media and transferred to an electroporation cuvette with a 0.4 cm gap between the electrodes (Bio-Rad #165-2088). One µg supercoiled H$_3$ receptor cDNA was added to the cells and mixed gently. The voltage for the electroporation was set at 0.25 kV and the capacitance was set at 960 µF. After electroporation the cells were diluted with 10 mL of complete media and were plated onto four 10 cm dishes at the following ratios: 1:20, 1:10, 1:5, and 1:2. The cells were allowed to recover for 24 h before adding 600 µg G-418. Colonies that survived selection were grown and tested. SK-N-MC cells were used because they give efficient coupling for inhibition of adenylate cyclase. The clones that gave the most robust inhibition of adenylate cyclase in response to histamine were used for further study.

B. [$^3$H]-N-Methylhistamine Binding

Cell pellets from histamine H$_3$ receptor-expressing SK-N-MC cells were homogenized in 50 mM TrisHCl/0.5 mM EDTA. Supernatants from an 800 g spin were collected and were recentrifuged at 30,000 g for 30 min. Pellets were re-homogenized in 50 mM Tris/5 mM EDTA (pH 7.4). Membranes were incubated with 0.8 nM [$^3$H]-N-methylhistamine plus/minus test compounds for 60 min at 25° C. and were harvested by rapid filtration over GF/C glass fiber filters (pre-treated with 0.3% polyethylenimine) followed by four washes with buffer. Filters were added to 5 mL of scintillation cocktail, and the signal was then counted on a liquid scintillation counter. Non-specific binding was defined with 10 µM histamine. pK$_i$ values were calculated based on a K$_D$ of 0.8 nM and a ligand concentration ([L]) of 0.8 nM according to the formula K$_i$=(IC$_{50}$)/(1+([L]/(KD)). Data for compounds tested in this assay are presented in Table 2 as an average of results obtained. Binding data for Comparative Example 1 was presented in U.S. patent application Ser. No. 10/690,115 (Oct. 21, 2003).

TABLE 2

| Binding Activity at the Human H$_3$ Receptor. | | |
|---|---|---|
| Ex. | K$_i$ (nM) | pK$_i$ |
| Example 1 | 5.4 | 8.3 |
| Example 1B | 6.5 | 8.2 |
| Example 2 | 2.0 | 8.7 |
| Example 2B | 2.0 | 8.7 |
| Example 3 | 2.5 | 8.6 |
| Example 4 | 6.0 | 8.2 |
| Example 4B | 23 | 7.6 |
| Comparative Example 2 | 1.0 | 9.0 |
| Comparative Example 2A | 1.7 | 8.8 |
| Comparative Example 2B | 2.0 | 8.7 |
| Comparative Example 3 | 2.0 | 8.7 |
| Comparative Example 3B | 1.0 | 9.0 |
| Comparative Example 4 | 0.7 | 9.2 |
| Comparative Example 5 | 1.0 | 9.0 |
| Comparative Example 6 | 6.0 | 8.2 |
| Comparative Example 6B | 5.0 | 8.3 |

C. Cyclic AMP Accumulation

Sublines of SK-N-MC cells were created that expressed a reporter construct and the human H$_3$ receptor. The pA$_2$ values were obtained as described by Barbier, A. J. et al. (Br. J. Pharmacol. 1994, 143 (5), 649-661). Data for compounds tested in this assay are presented in Table 3, as an average of the results obtained.

TABLE 3

Functional Activity

| Ex. | pA$_2$ |
| --- | --- |
| Example 1 | 8.4 |
| Example 2B | 9.0 |
| Comparative Example 1 | 9.0 |
| Comparative Example 1A | 8.9 |
| Comparative Example 2 | 9.5 |
| Comparative Example 3B | 9.6 |
| Comparative Example 4 | 10.0 |
| Comparative Example 6 | 8.2 |

D. Pharmacokinetics and Bioanalysis

One group of six male Sprague Dawley Rats (approx. 300 g body weight; three animals per time point) was used. They were group-housed, provided food and water ad libitum, and were maintained on a 12-h light and dark cycle. Animals were acclimatized for at least 7 days after receipt from the vendor prior to investigations.

For oral dosing, test compounds were formulated at 1 mg/mL in 0.5% hydroxypropyl methyl cellulose and delivered at a dose of 10 mg/kg. Citric acid salt forms (prepared as described for Example 1B) of the test compounds were used. Animals received a bolus dose of 10 mg/kg (10 mL/kg) for each compound via a 16 gauge intragastric gavage. For intravenous dosing, test compounds were formulated at 1 mg/mL in 5% dextrose in water and dosed at 1 mg/kg (1 mL/kg) with a bolus intravenous dose via a 24-gauge Terumo®Surflo® catheter in the lateral tail vein. All dosing solutions were prepared immediately prior to injection.

Blood samples (250 μL) were taken from the lateral tail vein into heparinized Natelson blood collection tubes and expelled into 1.5 mL mcirocentrifuge tubes. The blood samples were centrifuged for 5 min at 14,000 rpm in a microcentrifuge. Plasma was retained and kept in a −20° C. freezer until analysis by LC-MS/MS.

Data analysis was performed using WinNonlin version 3.3 or 4.0.1. A non-compartmental model (#200 for Extravascular administration and #201 for i.v.) was used to determine the pharmacokinetic parameters shown in Tables 4 and 5 (NA=not applicable or not determined).

TABLE 4

Pharmacokinetic Profiles in the Rat

| Ex. | Mode | $T_{max}$ (h) | $C_{max}$ (ng/mL) | $AUC_{INF}$ (h-ng/mL) | $T_{1/2}$ (h) | Cl (mL/min/kg) | $V_d$ (L/kg) |
| --- | --- | --- | --- | --- | --- | --- | --- |
| Ex. 1B | oral | 0.5 | 2787 | 8716 | 3.11 | 20.2 | 5.45 |
|  | i.v. | NA | 935 | 777 | 0.92 | 21.6 | 1.72 |
| Comp. Ex. 1B | oral | 1.5 | 1050 | 9743 | 4.71 | 17.1 | 6.98 |
|  | i.v. | NA | 4113 | 1560 | 3.2 | 12.8 | 3.55 |
| Comp. Ex. 2B | oral | 1.33 | 683 | 4104 | 2.89 | 43.2 | 10.33 |
|  | i.v. | NA | 285 | 464 | 1.86 | 34.8 | 6.41 |

TABLE 5

Pharmacokinetic Profiles in the Rat

| Ex. | Mode | $T_{max}$ (h) | $C_{max}$ (μmol/mL) | $AUC_{INF}$ (h-μmol/mL) | $T_{1/2}$ (h) | Cl (mL/min/kg) | $V_d$ (L/kg) |
| --- | --- | --- | --- | --- | --- | --- | --- |
| Ex. 2B | oral | 1.67 | 0.42 | 1.91 | 2.72 | 431 | 112 |
|  | i.v. | NA | 3.78 | 1.37 | 1.11 | 41.4 | 3.94 |
| Comp. Ex. 3B | oral | 1.33 | 0.16 | 1.95 | 8.22 | 270 | 180 |
|  | i.v. | NA | 1.49 | 1.16 | 7.60 | 44.2 | 29.2 |
| Comp. Ex. 4B | oral | 0.67 | 0.48 | 1.28 | 3.44 | 1135 | 397 |
|  | i.v. | NA | 0.46 | 0.41 | 2.08 | 113 | 20.3 |
| Ex. 3B | oral | 0.25 | 0.19 | 0.18 | 0.41 | NA | NA |
|  | i.v. | NA | 0.86 | 0.18 | 0.27 | 282 | 6.48 |
| Comp. Ex. 5B | oral | 0.38 | 0.07 | 0.12 | 0.95 | NA | NA |
|  | i.v. | NA | 2.68 | 0.42 | 1.33 | 154 | 17.8 |
| Ex. 4B | oral | 0.83 | 8.73 | 33.2 | 3.58 | NA | NA |
|  | i.v. | NA | 2.92 | 3.07 | 1.47 | 15.2 | 1.91 |
| Comp. Ex. 6B | oral | 0.50 | 2.96 | 19.99 | 4.35 | NA | NA |
|  | i.v. | NA | 1.41 | 1.34 | 2.36 | 34.9 | 7.04 |

What is claimed is:

1. A compound that is (4-cyclopropyl-piperazin-1-yl)-[4-(4-fluoro-piperidin-1-ylmethyl)-phenyl]-methanone, or enantiomers or pharmaceutically acceptable salts thereof.

2. A compound of claim 1 that is (4-cyclopropyl-piperazin-1-yl)-[4-(4-fluoro-piperidin-1-ylmethyl)-phenyl]-methanone or a pharmaceutically acceptable salt thereof.

3. A compound that is (4-cyclopropyl-piperazin-1-yl)-[4-(4-fluoro-piperidin-1-ylmethyl)-phenyl]-methanone citrate salt.

4. A pharmaceutical composition comprising a pharmaceutically acceptable carrier and an effective amount of (4-cyclopropyl-piperazin-1-yl)-[4-(4-fluoro-piperidin-1-ylmethyl)-phenyl]-methanone, or enantiomers or pharmaceutically acceptable salts thereof.

5. A pharmaceutical composition according to claim 4, further comprising topiramate.

* * * * *